US006326499B1

(12) United States Patent
Belanger

(10) Patent No.: US 6,326,499 B1
(45) Date of Patent: Dec. 4, 2001

(54) OMEGA CHAIN MODIFIED 15-HYDROXYEICOSATETRAENOIC ACID DERIVATIVES AND METHODS OF THEIR USE FOR THE TREATMENT OF DRY EYE

(75) Inventor: David B. Belanger, Fort Worth, TX (US)

(73) Assignee: Alcon Universal Ltd., Hunenberg (CH)

(*) Notice: Subject to any disclaimer, the term of this patent is extended or adjusted under 35 U.S.C. 154(b) by 0 days.

(21) Appl. No.: 09/694,144

(22) Filed: Oct. 23, 2000

Related U.S. Application Data
(60) Provisional application No. 60/164,375, filed on Nov. 9, 1999, and provisional application No. 60/211,587, filed on Jun. 15, 2000.

(51) Int. Cl.$^7$ ............................................. C07D 257/00
(52) U.S. Cl. ..................... 548/252; 548/250; 564/509; 568/31; 568/626; 568/662; 568/671; 568/673; 568/675; 568/927; 554/61; 554/213; 554/218
(58) Field of Search ...................... 554/61, 213, 218; 568/31, 626, 662, 671, 673, 675, 927; 564/509; 548/250, 252

(56) References Cited

U.S. PATENT DOCUMENTS

| | | | |
|---|---|---|---|
| 3,991,759 | 11/1976 | Urquhart | 128/260 |
| 4,131,651 | 12/1978 | Shah et al. | 424/78 |
| 4,370,325 | 1/1983 | Packman | 424/245 |
| 4,409,205 | 10/1983 | Shively | 424/78 |
| 4,421,748 | 12/1983 | Trager et al. | 424/199 |
| 4,744,980 | 5/1988 | Holly | 424/78 |
| 4,753,945 | 6/1988 | Gilbard et al. | 514/263 |
| 4,804,539 | 2/1989 | Guo et al. | 424/450 |
| 4,818,537 | 4/1989 | Guo | 424/427 |
| 4,868,154 | 9/1989 | Gilbard et al. | 514/13 |
| 4,883,658 | 11/1989 | Holly | 424/80 |
| 4,906,467 | 3/1990 | Schwartzman et al. | 424/80 |
| 4,914,088 | 4/1990 | Glonek et al. | 514/76 |
| 4,921,644 | 5/1990 | Lau et al. | 264/4.1 |
| 4,923,700 | 5/1990 | Kaufman | 424/427 |
| 4,966,773 | 10/1990 | Gressel et al. | 424/489 |
| 5,041,434 | 8/1991 | Lubkin | 514/182 |
| 5,064,655 | 11/1991 | Uster et al. | 424/450 |
| 5,075,104 | 12/1991 | Gressel et al. | 424/78.04 |
| 5,174,988 | 12/1992 | Mautone et al. | 424/45 |
| 5,278,151 | 1/1994 | Korb et al. | 514/76 |
| 5,290,572 | 3/1994 | MacKeen | 424/602 |
| 5,294,607 | 3/1994 | Glonek et al. | 514/76 |
| 5,306,483 | 4/1994 | Mautone | 424/45 |
| 5,358,706 | 10/1994 | Marlin et al. | 424/78.04 |
| 5,371,108 | 12/1994 | Korb et al. | 514/762 |
| 5,389,383 | 2/1995 | Huth | 424/650 |
| 5,403,598 | 4/1995 | Beck et al. | 424/717 |
| 5,403,841 | 4/1995 | Lang et al. | 514/226.8 |
| 5,455,265 | 10/1995 | Chandraratna | 514/448 |
| 5,578,586 | 11/1996 | Glonek et al. | 514/76 |
| 5,620,921 | 4/1997 | Sullivan | 514/178 |
| 5,696,166 | 12/1997 | Yanni et al. | 514/573 |
| 5,800,807 | 9/1998 | Hu et al. | 424/78.04 |

FOREIGN PATENT DOCUMENTS

| | | |
|---|---|---|
| 1 251 736 | 3/1989 | (CA). |
| 0 097 059 A2 | 12/1983 | (EP). |
| 0 132 089 A1 | 1/1985 | (EP). |
| WO 91/12808 | 9/1991 | (WO). |
| WO 92/04905 | 4/1992 | (WO). |

OTHER PUBLICATIONS

Lang et al., "Antimicrobial Effects of Biosurfactants," *Fett Wissenschaft Technologie*, vol. 91(9), pp. 363–366 (1989).
Alpert et al., "Human Tracheal Epithelial Cells Selectively Incorporate 15–Hydroxyeicosatetraenoic Acid into Phosphatidylinositol," *Am. J. Respir. Cell Mol. Biol.*, vol. 8, pp. 273–281 (1993).
Corfield et al., "Ocular Mucins: Purification, Metabolism and Functions," *Prog Retinal Eye Res.*, vol. 16, pp. 627–656 (1997).
Danjo et al., "Alternation of Mucin in Human Conjunctival Epithelia in Dry Eye," *Invest Ophthalmol Vis. Sci.*, vol. 39; pp. 2602–2609 (1998).
Dartt et. al., Vasoactive intestinal peptide–stimulated glycocongjugate secretion from conjunctival goblet cells. Experimental Eye Research, vol. 63, pp. 27–34, (1996).
Dilly et al., "Surface Changes in the Anesthetic Conjunctiva in Man, with Special Reference to the Production of Mucus from a Non–Goblet–Cell Source," *British Journal of Ophthalmology*, vol. 65; pp. 833–842 (1981).
Dohlman, "Symposium on the Dry Eye, New Concepts in Ocular Xerosis," *Ophthalmological Societies of the United Kingdom*, vol. XCI; pp. 105–118 (1971).
Glasgow et al., "Tear lipocalins bind a broad array of lipid ligands," *Current Eye Research*, vol. 14(5), pp. 363–372 (1995).
Graber et al., 15–Hydroxyeicosatetraenoic Acid Stimulates Migration of Human Retinal Microvessel Endothelium In Vitro and Neovascularization In Vivo, *Prostaglandins*, vol. 39 (6); pp. 665–673 (1990).
Greiner et al., "Histochemical Analysis of Secretory Vesicles in Non–Goblet Conjunctival Epithelial Cells," *Acta Ophthalmol.*, vol. 63; pp. 89–92 (1985).
Greiner et al., Meibomian gland phospholipids, *Current Eye Research*, vol. 15(4); pp. 371–375 (1996).
Greiner et al., "Mucus Secretory Vesicles in Conjunctival Epithelial Cells of Wearers of Contact Lenses," *Arch Ophthalmol.*, vol. 98; pp. 1843–1846 (1980).
Greiner et al., "Phospholipids in Meibomian Gland Secretion," *Ophthalmic Res.*, vol. 28, pp. 44–49 (1996).
Hamberg et al., "Identification of 15–hydroxy–5.8.11.13–eicosatetraenoic acid (15–HETE) as a major metabolite of arachidonic acid in human lung," *Acta Physical Scand.*, vol. 110; pp. 219–221 (1980).
Holly et al., "Tear Physiology and Dry Eyes," *Surv. Ophthalmol.*, vol. 22; pp. 69–87 (1977).

(List continued on next page.)

*Primary Examiner*—Deborah D. Carr
(74) *Attorney, Agent, or Firm*—Patrick M. Ryan

(57) ABSTRACT

Omega chain modified 15-HETE derivatives and methods of their use for treating dry eye are disclosed.

4 Claims, No Drawings

OTHER PUBLICATIONS

Holzfeind et al., "The Human Lacrimal Gland Synthesizes Apolipoprotein D mRNA in Addition to Tear Prealbumin mRNA, Both Species Encoding Members of the Lipocalin Superfamily," *Exp. Eye Res.*, vol. 65, pp. 495–500 (1995).

Hutchinson, "Arachidonate 15–lipoxygenase; characteristics and potential biological significance," *Eicosanoids*, vol. 4, pp. 65–74 (1991).

Inatomi et al., "Human Corneal and Conjunctival Epithelia Express MUC1 Mucin," *Invest Ophthalmol Vis Sci.*, vol. 36; pp. 1818–1827 (1995).

Jansen et al., "Phospholipids Chiral at Phosphorus. Synthesis and Stereospecificity of Phosphorothioate Analogues of Platelet–Activating Factor," *Biochemistry*, vol. 27, pp. 4619–4624 (1998).

Johnson et al., 15–Hydroxyeicosatetraenoic Acid is a Potent Inflammatory Mediator and Agonist of Canine Tracheal Mucus Secretion, from the Hypersensitivity Diseases Research, Lipids Research. The Upjohn Company, Kalamazoo, Michigan, pp. 917–922 (1984).

Kessing et al., "Mucous Gland System of the Conjunctiva," *Acta Ophthalmol.* Suppl., vol. 95; pp. 1–133 (1968).

Korb et al., Tear Film Lipid Layer Formation: Implications for Contact Lens Wear, *Optometry and Vision Science*, vol. 73(3), pp. 189–192 (1996).

Legrand et al., "Substitution of 15–Hydroxyeicosatetraenoic Acid in the Phosphoinositide Signaling Pathway," *J. of Biological Chemistry*, vol. 266 (12), pp. 7570–7577 (1991).

Lemp et al., "Report of the National Eye Institute/Industry Workshop on Clinical Trials in Dry Eyes," *CLAO*, vol. 21(4), pp. 221–231 (1995).

Lemp, "Tear Substitutes in the Treatment of Dry Eyes," *External Ocular Diseases: Diagnosis and Current Therapy*, Laibson and Trobe (ed.) Little, Brown and Company, Boston; vol. 13(4); pp. 145–153 (1973).

Marom et al., "Effects of Arachidonic Acid, Monohydroxyeicosatetraenoic Acid and Prostaglandins on the Release of Mucous Glycoproteins from Human Airways In Vitro," *The J. of Clinical Investigation*, vol. 67; pp. 1695–1702 (1981).

Marom et al., "Human Airway Monohydroxyeicosatetraenoic Acid Generation and Mucus Release," *Journal of Clinical Investigation*, vol. 72, pp. 122–127 (1983).

Masferrer et al., "12(R)–Hydroxyeicosatetraenoic Acid, An Endogenous corneal Arachidonate Metabolite, Lowers Intraocular Pressure in Rabbits," *Investigative Ophthalmology and Visual Science*, vol. 31(3); pp. 535–539 (1990).

McCulley et al., "Tear Film Structure and Dry Eyes," *Contactologia*, vol. 20, pp. 145–149 (1998).

Mysore et al., "Controlled Ocular Drug Delivery and Vesicular Systems: An Overview," *Indian Drugs*, vol. 33(9), pp. 431–442 (1996).

Nakamura et. al., "Gefarnate stimulates secretion of mucin–like glycoproteins by corneal epithelium in vitro and protects corneal epithelium from dessication in vivo," *Experimental Eye Research*, vol. 65, pp. 569–574 (1997).

Nicolau et al., "Total Synthesis of 5(S), 15(S)–Dihydroxy–6, 13–trans–8,11–cis–eicosatetraenoic Acid (5,15–DiHETE) and 8(S), 15(S)–Dihydroxy–5,11–cis–9,13–trans–eicosatetraenoic Acid (8,15–DiHETE): Two Novel Metabolites of Arachidonic Acid," *J. Am. Chem. Soc.*, vol. 106, p. 5734 (1984).

Ohno, M.; Otsuka, M. Organic Reactions, vol. 37, p. 1 (1989).

Ohyama et al., "Sensitive Densitometry for the Determination of Platelet–activating Factor and Other Phospholipids in Human Tears," *Analyst*, vol. 121, pp. 1943–1947 (1996).

Pleyer et al., "Analysis of Interactions Between the Corneal Epithelium and Liposomes Qualitative and Quantitative Fluorescence Studies of a Corneal Epithelial Cell Line," *Survey of Ophthalmology.*, vol. 39 (Supl. 1), S3–S16 (1995).

Profita et al., "Interleukin–4 Enhances 15–Lipoxygenase Activity and Incorporation of 15(S)–HETE into Cellular Phospholipids in Cultured Pulmonary Epithelial Cells," *Am. J. Respir. Cell Mol. Biol.*, vol. 20, pp. 61–68 (1999).

Prydal et al., "Study of Human Tear Film Thickness and Structure Using Laser Interferometry," *Invest Ophthalmol Vis Sci.*, vol. 33; pp. 2006–2011 (1992).

Shelhamer et al., "The Effects of Arachinoids and Leukotrienes on the Release of Mucus from Human Airways," *Chest Supplement*, 24th Aspen Lung Conference, vol. 81(5); pp. 36S–37S (1982).

Shigemitsu et al., "Effects of Mucin Ophthalmic Solution on Epithelial Wound Healing in Rabbit Cornea," *Ophthalmic Res.*, vol. 29; pp. 61–66 (1997).

Shine et al., Keratoconjunctivitis Sicca Associated with Meibomian Secretion Polar Lipid Abnormality, *Arch. Ophthalmology*, vol. 116, pp. 849–852 (1998).

Watanabe et al., "Human Corneal and Conjunctival Epithelia Produce a Mucin–like Glycoprotein for the Apical Surface," *Invest Ophthalmol Vis Sci.*, vol. 36; pp. 337–344 (1995).

Wiggins et al., "12(S)–Hydroxy–5,8.10.14–Eicosatetraenoic Acid is a More Potent Neutrophil Chemoattractant Than the 12(R) Epimer in the Rat Cornea," *Prostaglandins*, vol. 49(2) pp. 131–141 (1990).

Yanni et al. ,"Effect of Intravenously Administered Lipoxygenase Metabolites on Rat Tracheal Mucous Gel Layer Thickness," *Int Arch Allergy Appl Immunol*, vol. 90 pp. 307–309 (1989).

Yu et al., "Effect of Polar Head Groups on the Interactions of Phospholipase $A_2$ with Phosphonate Transition–State Analogues," *Biochemistry*, vol. 32, pp. 10185–10192.

Zhang et al., "Enzymatic Asymmetric Hydroxylation of Pentadienols Using Soybean Lipoxygenase," *J. Am. Chem. Soc.*, vol. 111(26), pp. 9241–9242 (1989).

Zhu et al., Synthesis of Phospholipids Bearing a Conjugated Oxo–polyunsaturated Fatty Acid Residue, J. Chem. Research (S)., vol. 8, pp. 500–501 (1999).

OMEGA CHAIN MODIFIED 15-HYDROXYEICOSATETRAENOIC ACID DERIVATIVES AND METHODS OF THEIR USE FOR THE TREATMENT OF DRY EYE

This application claims priority to co-pending U.S. Provisional Applications, Serial No. 60/164,375 filed Nov. 9, 1999, and 60/211,587, filed Jun. 15, 2000.

The present invention is directed to compositions containing certain 15-hydroxyeicosatetraenoic acid derivatives and methods for their use in treating dry eye.

BACKGROUND OF THE INVENTION

Dry eye, also known generically as keratoconjunctivitis sicca, is a common ophthalmological disorder affecting millions of Americans each year (Schein et. al., Prevalence of dry eye among the elderly. *American J. Ophthalmology*, 124:723–738, (1997)). The condition is particularly widespread among post-menopausal women due to hormonal changes following the cessation of fertility. Dry eye may afflict an individual with varying severity. In mild cases, a patient may experience burning, a feeling of dryness, and persistent irritation such as is often caused by small bodies lodging between the eye lid and the eye surface. In severe cases, vision may be substantially impaired. Other diseases, such as Sjogren's disease and cicatricial pemphigoid manifest dry eye complications.

Although it appears that dry eye may result from a number of unrelated pathogenic causes, all presentations of the complication share a common effect, that is the breakdown of the pre-ocular tear film, which results in dehydration of the exposed outer surface and many of the symptoms outlined above (Lemp, Report of the Nation Eye Institute/Industry Workshop on Clinical Trials in Dry Eyes, *The CLAO Journal*, volume 21, number 4, pages 221–231 (1995)). Four events have been identified which singly or in combination are believed to result in the dry eye condition: a) decreased tear production or increased tear evaporation; b) decreased conjunctival goblet-cell density; c) increased corneal desquamation; and d) destabilization of the cornea-tear interface (Gilbard, Dry eye: pharmacological approaches, effects, and progress. *The CLAO Journal*, (22:141–145 (1996)). Another major problem is the decreased mucin production by the conjunctival cells and/or corneal epithelial cells of mucin, which protects and lubricates the ocular surface (Gipson and Inatomi, Mucin genes expressed by ocular surface epithelium. *Progress in Retinal and Eye Research*, 16:81–98 (1997)).

Practitioners have taken several approaches to the treatment of dry eye. One common approach has been to supplement and stabilize the ocular tear film using so-called artificial tears instilled throughout the day. Another approach has been the use of ocular inserts that provide a tear substitute or to stimulate endogenous tear production.

Examples of the tear substitution approach include the use of buffered, isotonic saline solutions, aqueous solutions containing water soluble polymers that render the solutions more viscous and thus less easily shed by the eye. Tear reconstitution is also attempted by providing one or more components of the tear film such as phospholipids and oils. Examples of these treatment approaches are disclosed in U.S. Pat. Nos. 4,131,651 (Shah et al.), U.S. Pat. No. 4,370,325 (Packman), U.S. Pat. No. 4,409,205 (Shively), U.S. Pat. No. 4,744,980 and U.S. Pat. No. 4,883,658 (Holly), U.S. Pat. No. 4,914,088 (Glonek), U.S. Pat. No. 5,075,104 (Gressel et al.) and U.S. Pat. No. 5,294,607 (Glonek et al.).

United States Patents directed to the use of ocular inserts in the treatment of dry eye include U.S. Pat. No. 3,991,759 (Urquhart). Other semi-solid therapy has included the administration of carrageenans (U.S. Pat. No. 5,403,841, Lang) which gel upon contact with naturally occurring tear film.

Another recent approach involves the provision of lubricating substances in lieu of artificial tears. U.S. Pat. No. 4,818,537 (Guo) discloses the use of a lubricating, liposome-based composition.

Aside from the above efforts, which are directed primarily to the alleviation of symptoms associated with dry eye, methods and compositions directed to treatment of the dry eye condition have also been pursued. For example, U.S. Pat. No. 5,041,434 (Lubkin) discloses the use of sex steroids, such as conjugated estrogens, to treat dry eye condition in post-menopausal women; U.S. Pat. No. 5,290,572 (MacKeen) discloses the use of finely divided calcium ion compositions to stimulate preocular tear film; and U.S. Pat. No. 4,966,773 (Gressel et al.) discloses the use of microfine particles of one or more retinoids for ocular tissue normalization.

Although these approaches have met with some success, problems in the treatment of dry eye nevertheless remain. The use of tear substitutes, while temporarily effective, generally requires repeated application over the course of a patient's waking hours. It is not uncommon for a patient to have to apply artificial tear solution ten to twenty times over the course of the day. Such an undertaking is not only cumbersome and time consuming, but is also potentially very expensive. Transient symptoms of dry eye associated with refractive surgery have been reported to last in some cases from six weeks to six months or more following surgery.

The use of ocular inserts is also problematic. Aside from cost, they are often unwieldy and uncomfortable. Further, as foreign bodies introduced in the eye, they can be a source of contamination leading to infections. In situations where the insert does not itself produce and deliver a tear film, artificial tears must still be delivered on a regular and frequent basis.

In view of the foregoing, there is a clear need for an effective treatment for dry eye that is capable of alleviating symptoms, as well as treating the underlying physical and physiological deficiencies of dry eye, and that is both convenient and inexpensive to administer.

Mucins are proteins which are heavily glycosylated with glucosamine-based moieties. Mucins provide protective and lubricating effects to epithelial cells, especially those of mucosal membranes. Mucins have been shown to be secreted by vesicles and discharged on the surface of the conjuctival epithelium of human eyes (Greiner et al., Mucus Secretory Vesicles in Conjunctival Epithelial Cells of Wearers of Contact Lenses, *Archives of Ophthalmology*, volume 98, pages 1843–1846 (1980); and Dilly et al., Surface Changes in the Anaesthetic Conjunctiva in Man, with Special Reference to the Production of Mucus from a Non-Goblet-Cell Source, *British Journal of Ophthalmology*, volume 65, pages 833–842 (1981)). A number of human-derived mucins which reside in the apical and subapical corneal epithelium have been discovered and cloned (Watanabe et al., Human Corneal and Conjuctival Epithelia Produce a Mucin-Like Glycoprotein for the Apical Surface, *Investigative Ophthalmology and Visual Science*, volume 36, number 2, pages 337–344 (1995)). Recently, Watanabe discovered a new mucin which is secreted via the cornea apical and subapical cells as well as the conjunctival epithelium of the human eye (Watanabe et al., *IOVS*, volume 36, number 2, pages 337–344 (1995)). These mucins provide lubrication, and additionally attract and hold moisture and sebacious material for lubrication and the corneal refraction of light.

Mucins are also produced and secreted in other parts of the body including lung airway passages, and more specifically from goblet cells interspersed among tracheal/bronchial epithelial cells. Certain arachidonic acid metabolites have been shown to stimulate mucin production in these cells. Yanni reported the increased secretion of mucosal glycoproteins in rat lung by hydroxyeicosatetraenoic acid ("HETE") derivatives (Yanni et al, Effect of Intravenously Administered Lipoxygenase Metabolites on Rat Trachael Mucous Gel Layer Thickness, *International Archives of Allergy And Applied Immunology*, volume 90, pages 307–309 (1989)). Similarly, Marom has reported the production of mucosal glycoproteins in human lung by HETE derivatives (Marom et al., Human Airway Monohydroxy-eicosatetraenoic Acid Generation and Mucus Release, *Journal of Clinical Investigation*, volume 72, pages 122–127 (1983)). Nowhere in the art, however, has the use of HETE derivatives been proposed to stimulate mucin production in ocular tissues as a treatment for dry eye.

The conventional treatment for dry eye, as discussed above, includes administration of artificial tears to the eye several times a day. Other agents claimed for increasing ocular mucin and/or tear production include vasoactive intestinal polypeptide (Dartt et. al., Vasoactive intestinal peptide-stimulated glycocongiugate secretion from conjunctival goblet cells. *Experimental Eye Research*, 63:27–34, (1996)), gefarnate (Nakmura et. al., Gefarnate stimulates secretion of mucin-like glycoproteins by corneal epithelium in vitro and protects corn eal epithelium from dessication in vivo, *Experimental Eye Research*, 65:569–574 (1997)), and the use of liposomes (U.S. Pat. No. 4,818,537), androgens (U.S. Pat. No. 5,620,921), melanocycte stimulating hormones (U.S. Pat. No. 4,868,154), and phosphodiesterase inhibitors (U.S. Pat. No. 4,753,945), retinoids (U.S. Pat. No. 5,455,265). However, many of these compounds or treatments suffer from a lack of specificity, efficacy and potency and none of these agents have been marketed so far as therapeutically useful products to treat dry eye and related ocular surface diseases. Of particular relevance to the present invention is the claimed use of hydroxyeicosatetraenoic acid derivatives to treat dry eye (U.S. Pat. No. 5,696,166). Thus, there remains a need for an efficacious therapy for the treatment of dry eye and related diseases.

SUMMARY OF THE INVENTION

The present invention is directed to compositions and methods for the treatment of dry eye and other disorders requiring the wetting of the eye, including symptoms of dry eye associated with refractive surgery such as LASIK surgery. More specifically, the present invention discloses derivatives of (5Z,8Z,11Z,13E)-15-hydroxyeicosa-5,8,11,14-tetraenoic acid (15-HETE) in which the ω-chain is modified as to inhibit metabolic oxidation at C-15, and methods using the same for treating dry eye type disorders. The compositions are preferably administered topically to the eye.

DETAILED DESCRIPTION OF THE INVENTION

The ω-chain modified 15-HETE derivatives of the present invention are those of formula I:

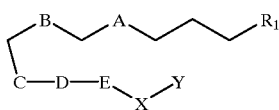

wherein:
$R^1$ is $CO_2R$, $CONR^2R^3$, $CH_2OR^4$, $CH_2NR^5R^6$, $CH_2N_3$, $CH_2Hal$, $CH_2NO_2$, $CH_2SR^{20}$, $COSR^{21}$, or 2,3,4,5-tetrazol-1-yl, where:
  R is H or a pharmaceutically acceptable cation, or $CO_2R$ forms a pharmaecutically acceptable ester moicty;
  $NR^2R^3$, $NR^5R^6$ are the same or different and comprise a free or functionally modified amino group;
  $OR^4$ comprises a free or functionally modified hydroxy group; Hal is F, Cl, Br, or I;
  $SR^{20}$ comprises a free or functionally modified thiol group;
  $R^{21}$ is H or a pharmaceutically acceptable cation, or $COSR^{21}$ forms a pharmaceutically acceptable thioester moiety;
A, B, C, D are the same or different and are $C_1$–$C_5$ alkyl, $C_2$–$C_5$ alkenyl, $C_{1-5}$ cyclopropyl, $C_2$–$C_5$ alkynyl, or a $C_3$–$C_5$ allenyl group;
E is

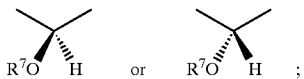

where $OR^7$ comprises a free or functionally modified hydroxy group;
$X=(CH_2)_m$ or $(CH_2)_mO$, where m=1–6; and
Y=a phenyl ring optionally substituted with alkyl, halo, trihalomethyl, acyl, or a free or functionally modified hydroxy, amino, or thiol group; or
$X—Y=(CH_2)_pY^1$; where p=0–6; and

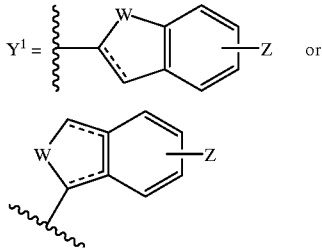

wherein:
$W=CH_2$, O, $S(O)_q$, $NR^8$, $CH_2CH_2$, CH=CH, $CH_2O$, $CH_2S(O)_q$, CH=N, or $CH_2NR^8$; where q=0–2, and $R^8$=H, alkyl, or acyl;
Z=H, alkyl, acyl, halo, trihalomethyl, or a free or functionally modified amino, thiol, or hydroxy group; and
----=single or double bond;
or X—Y=cyclohexyl.

To the best of our knowledge none of the compounds of the present invention have been previously reported in the literature.

Included within the scope of the present invention are the individual enantiomers of the title compounds, as well as their racemic and non-racemic mixtures. The individual enantiomers can be enantioselectively synthesized from the appropriate enantiomerically pure or enriched starting material by means such as those described below. Alternatively, they may be enantioselectively synthesized from racemic/non-racemic or achiral starting materials. (*Asymmetric Synthesis*; J. D. Morrison and J. W. Scott, Eds.; Academic Press Publishers: New York, 1983–1985, volumes 1–5; *Principles of Asymmetric Synthesis*; R. E. Gawley and J. Aube, Eds.; Elsevier Publishers: Amsterdam, 1996). They may also be isolated from racemic and non-racemic mixtures by a number of known methods, e.g. by purification of a sample by chiral HPLC (*A Practical Guide to Chiral Separations by HPLC*; G. Subramanian, Ed.; VCH Publishers: New York, 1994; *Chiral Separations by HPLC*; A. M. Krstulovic, Ed.; Ellis Horwood Ltd. Publishers, 1989), or by enantioselective hydrolysis of a carboxylic acid ester sample by an enzyme (Ohno, M.; Otsuka, M. *Organic Reactions*, volume 37, page 1 (1989)). Those skilled in the art will appreciate that racemic and non-racemic mixtures may be obtained by several means, including without limitation, nonenantioselective synthesis, partial resolution, or even mixing samples having different enantiomeric ratios. Departures may be made from such details within the scope of the accompanying claims without departing from the principles of the invention and without sacrificing its advantages. Also included within the scope of the present invention are the individual isomers substantially free of their respective enantiomers.

As used herein, the terms "pharmaceutically acceptable cationic salt"/"pharmaceutically acceptable ester moiety/pharmaceutically acceptable thioester moiety" means any cationic salt/ester/thioester moiety that would be suitable for therapeutic administration to a patient by any conventional means without significant deleterious health consequences; and "ophthalmically acceptable cationic salt"/"ophthalmically acceptable ester/ophthalmically acceptable thioester moiety" means any pharmaceutically acceptable cationic salt/ester/thioester moiety that would be suitable for ophthalmic application, i.e. non-toxic and non-irritating. Wavy line attachments indicate that the configuration may be either alpha ($\alpha$) or beta ($\beta$). Hatched lines indicate the $\alpha$ configuration. A solid triangular line indicates the $\beta$ configuration.

The term "free hydroxy group" means an OH. The term "functionally modified hydroxy group" means an OH which has been functionalized to form: an ether, in which an alkyl, aryl, cycloalkyl, hetcrocycloalkyl, alkenyl, cycloalkenyl, heterocycloalkenyl, alkynyl, or heteroaryl group is substituted for the hydrogen; an ester, in which an acyl group is substituted for the hydrogen; a carbamate, in which an aminocarbonyl group is substituted for the hydrogen; or a carbonate, in which an aryloxy-, heteroaryloxy-, alkoxy-, cycloalkoxy-, heterocycloalkoxy-, alkenyloxy-, cycloalkenyloxy-, heterocycloalkenyloxy-, or alkynyloxy-carbonyl group is substituted for the hydrogen. Preferred moieties include OH, $OCH_2C(O)CH_3$, $OCH_2C(O)C_2H_5$, $OCH_3$, $OCH_2CH_3$, $OC(O)CH_3$, and $OC(O)C_2H_5$.

The term "free amino group" means an $NH_2$. The term "functionally modified amino group" means an $NH_2$ which has been functionalized to form: an aryloxy-, heteroaryloxy-, alkoxy-, cycloalkoxy-, heterocycloalkoxy-, alkenyl-, cycloalkenyl-, heterocycloalkenyl-, alkynyl, or hydroxyamino group, where the appropriate group is substituted for one of the hydrogens; an aryl-, heteroaryl-, alkyl-, cycloalkyl-, heterocycloalkyl-, alkenyl-, cycloalkenyl-, heterocycloalkenyl-, or alkynylamino group, where the appropriate group is substituted for one or both of the hydrogens; an amide, in which an acyl group is substituted for one of the hydrogens; a carbamate, in which an an aryloxy-, heteroaryloxy-, alkoxy-, cycloalkoxy-, heterocycloalkoxy-, alkenyl-, cycloalkenyl-, heterocycloalkenyl-, or alkynylcarbonyl group is substituted for one of the hydrogens; or a urea, in which an aminocarbonyl group is substituted for one of the hydrogens. Combinations of these substitution patterns, for example an $NH_2$ in which one of the hydrogens is replaced by an alkyl group and the other hydrogen is replaced by an alkoxycarbonyl group, also fall under the definition of a functionally modified amino group and are included within the scope of the present invention. Preferred moieties include $NH_2$, $NHCH_3$, $NHC_2H_5$, $N(CH_3)_2$, $NHC(O)CH_3$, $NHOH$, and $NH(OCH_3)$.

The term "free thiol group" means an SH. The term "functionally modified thiol group" means an SH which has been functionalized to form: a thioether, where an alkyl, aryl, cycloalkyl, heterocycloalkyl, alkenyl, cycloalkenyl, heterocycloalkenyl, alkynyl, or heteroaryl group is substituted for the hydrogen; or a thioester, in which an acyl group is substituted for the hydrogen. Preferred moieities include SH, $SC(O)CH_3$, $SCH_3$, $SC_2H_5$, $SCH_2C(O)C_2H_5$, and $SCH_2C(O)CH_3$.

The term "acyl" represents a group that is linked by a carbon atom that has a double bond to an oxygen atom and a single bond to another carbon atom.

The term "alkyl" includes straight or branched chain aliphatic hydrocarbon groups that are saturated and have 1 to 15 carbon atoms. The alkyl groups may be interrupted by one or more heteroatoms, such as oxygen, nitrogen, or sulfur, and may be substituted with other groups, such as halogen, hydroxyl, aryl, cycloalkyl, aryloxy, or alkoxy. Preferred straight or branched alkyl groups include methyl, ethyl, propyl, isopropyl, butyl and t-butyl.

The term "cycloalkyl" includes straight or branched chain, saturated or unsaturated aliphatic hydrocarbon groups which connect to form one or more rings, which can be fused or isolated. The rings may be substituted with other groups, such as halogen, hydroxyl, aryl, aryloxy, alkoxy, or lower alkyl. Preferred cycloalkyl groups include cyclopropyl, cyclobutyl, cyclopentyl and cyclohexyl.

The term "$C_1$–$C_5$ cyclopropyl" means an alkyl chain of 1 to 5 carbon atoms containing a cyclopropyl group wherein the cyclopropyl group may start, be contained in or terminate the alkyl chain.

The term "heterocycloalkyl" refers to cycloalkyl rings that contain at least one heteroatom such as O, S, or N in the ring, and can be fused or isolated. The rings may be substituted with other groups, such as halogen, hydroxyl, aryl, aryloxy, alkoxy, or lower alkyl. Preferred heterocycloalkyl groups include pyrrolidinyl, tetrahydrofuranyl, piperazinyl, and tetrahydropyranyl.

The term "alkenyl" includes straight or branched chain hydrocarbon groups having 1 to 15 carbon atoms with at least one carbon-carbon double bond, the chain being optionally interrupted by one or more heteroatoms. The chain hydrogens may be substituted with other groups, such as halogen. Preferred straight or branched alkeny groups include, allyl, 1-butenyl, 1-methyl-2-propenyl and 4-pentenyl.

The term "cycloalkenyl" includes straight or branched chain, saturated or unsaturated aliphatic hydrocarbon groups which connect to form one or more nonaromatic rings containing a carbon-carbon double bond, which can be fused or isolated. The rings may be substituted with other groups, such as halogen, hydroxyl, alkoxy, or lower alkyl. Preferred cycloalkenyl groups include cyclopentenyl and cyclohexenyl.

The term "heterocycloalkenyl" refers to cycloalkenyl rings which contain one or more heteroatoms such as O, N, or S in the ring, and can be fused or isolated. The rings may be substituted with other groups, such as halogen, hydroxyl, aryl, aryloxy, alkoxy, or lower alkyl. Preferred heterocycloalkenyl groups include pyrrolidinyl, dihydropyranyl, and dihydrofuranyl.

The term "carbonyl group" represents a carbon atom double bonded to an oxygen atom, wherein the carbon atom has two free valencies.

The term "aminocarbonyl" represents a free or functionally modified amino group bonded from its nitrogen atom to the carbon atom of a carbonyl group, the carbonyl group itself being bonded to another atom through its carbon atom.

The term "lower alkyl" represents alkyl groups containing one to six carbons ($C_1$–$C_6$).

The term "halogen" represents fluoro, chloro, bromo, or iodo.

The term "aryl" refers to carbon-based rings which are aromatic. The rings may be isolated, such as phenyl, or fused, such as naphthyl. The ring hydrogens may be substituted with other groups, such as lower alkyl, halogen, free or functionalized hydroxy, trihalomethyl, etc. Preferred aryl groups include phenyl, 3-(trifluoromethyl)phenyl, 3-chlorophenyl, and 4-fluorophenyl.

The term "heteroaryl" refers to aromatic hydrocarbon rings which contain at least one heteroatom such as O, S, or N in the ring. Heteroaryl rings may be isolated, with 5 to 6 ring atoms, or fused, with 8 to 10 atoms. The heteroaryl ring(s) hydrogens or heteroatoms with open valency may be substituted with other groups, such as lower alkyl or halogen. Examples of heteroaryl groups include imidazole, pyridine, indole, quinoline, furan, thiophene, pyrrole, tetrahydroquinoline, dihydrobenzofuran, and dihydrobenzindole.

The terms "aryloxy", "heteroaryloxy", "alkoxy", "cycloalkoxy", "heterocycloalkoxy", "alkenyloxy", "cycloalkenyloxy", "heterocycloalkenyloxy", and "alkynyloxy" represent an aryl, heteroaryl, alkyl, cycloalkyl, heterocycloalkyl, alkenyl, cycloalkenyl, heterocycloalkenyl, or alkynyl group attached through an oxygen linkage.

The terms "alkoxycarbonyl", "aryloxycarbonyl", "heteroaryloxycarbonyl", "cycloalkoxycarbonyl", "heterocycloalkoxycarbonyl", "alkenyloxycarbonyl", "cycloalkenyloxycarbonyl", "heterocycloalkenyloxycarbonyl", and "alkynyloxycarbonyl" represent an alkoxy, aryloxy, heteroaryloxy, cycloalkoxy, heterocycloalkoxy, alkenyloxy, cycloalkenyloxy, heterocycloalkenyloxy, or alkynyloxy group bonded from its oxygen atom to the carbon of a carbonyl group, the carbonyl group itself being bonded to another atom through its carbon atom.

Preferred compounds of the present invention include those of formula I, wherein:

$R^1$ is $CO_2R$, where R is H or an ophthalmically acceptable cationic salt, or $CO_2R$ forms an ophthalmically acceptable ester moiety;

A, B, C, D are the same or different and are $CH_2CH_2$, $CH=CH$, $C\equiv C$, or E is where $R^7$ is H or $CH_3$;
X is $CH_2CH_2$ or $CH_2O$; and
Y phenyl, optionally substituted with halo, trifluoromethyl, or a free or functionalized hydroxy group; or
X—Y=cyclohexyl; or

X—Y=$Y^1$,

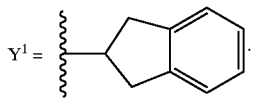

Among the especially preferred of the foregoing are compounds 1–4, whose preparations are detailed in the following examples 1–4:

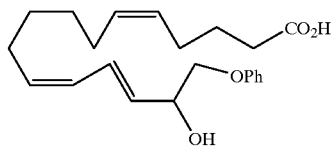

1
(5Z,11Z,13E)-(15RS)-15-hydroxy-16-phenoxy-17,18,19,20-tetranoreicosa-5,11,13-trienoic acid

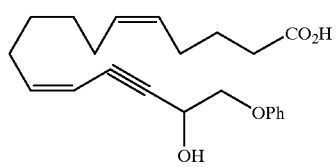

2
(5Z,11Z)-(15RS)-15-hydroxy-16-phenoxy-17,18,19,20-tetranoreicosa-5,11-dien-13-ynoic acid

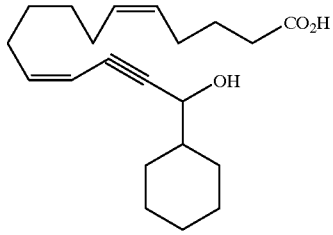

3
(5Z,11Z)-(15RS)-15-cyclohexyl-15-hydroxy-16,17,18,19,20-pentanoreicosa-5,11-dien-13-ynoic acid

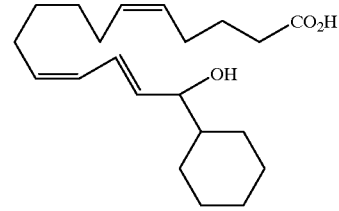

4
(5Z,11Z,13E)-(15RS)-15-cyclohexyl-15-hydroxy-16,17,18,19,20-pentanoreicosa-5,11,13-trienoic acid

EXAMPLE 1

Synthesis of 1

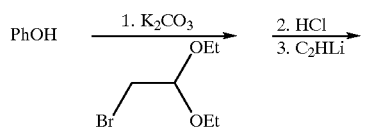

-continued

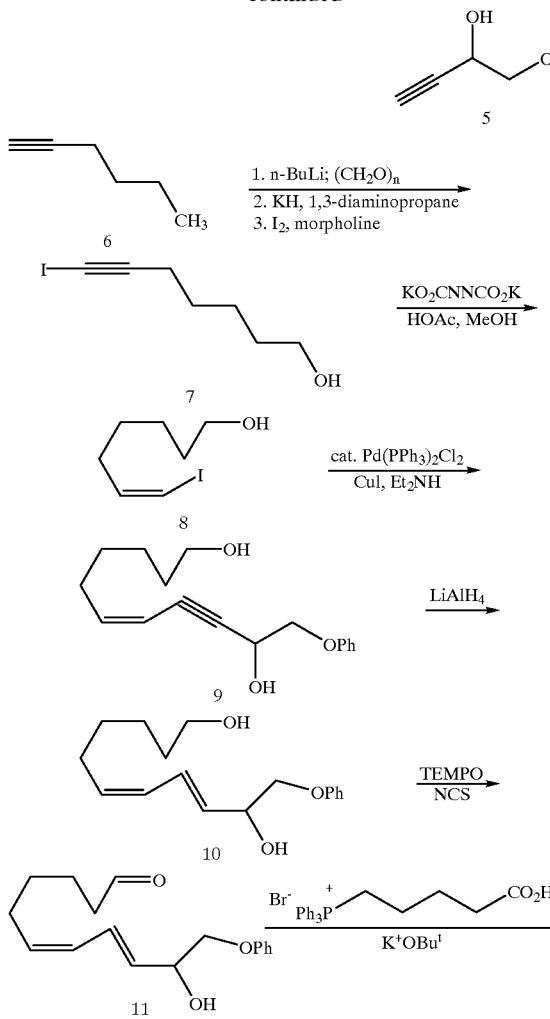

(5Z,11Z, 13E)-(15RS)-15-hydroxy-16-phenoxy-17,18,19,20-tetranoreicosa-5,11,13-trienoic acid (1)

Treatment of phenol with potassium carbonate and bromoacetaldehyde diethyl acetal provides phenoxyacetaldehyde diethyl acetal. Treatment with aqueous HCl followed by addition of the intermediate aldehyde to a −78° C. solution of ethynyl lithium affords alkyne 5. Treatment of 1-hexyne (6) with n-BuLi and paraformaldehyde affords an intermediate propargyl alcohol, which is treated sequentially with KH/1,3-diaminopropane and I$_2$/morpholine to afford iodoalkyne 7. Reduction of 7 with dipotassium azodicarboxylate/acetic acid in methanol provides the cis-vinyl iodide 8. Palladium-catalyzed coupling of 8 and propargyl alcohol 5 gives enynediol 9. Reduction of 9 with LiAlH$_4$ yields diol 10, which is oxidized to aldehyde II using catalytic 2,2,6,6-tetramethylpiperidinoxyl free radical (TEMPO) and stoichiometric N-chlorosuccinimide (NCS). Wittig condensation of 11 with (4-carboxybutyl) triphenylphosphonium bromide in the presence of potassium t-butoxide (KOBu$^t$) affords 1.

EXAMPLE 2

Synthesis of 2

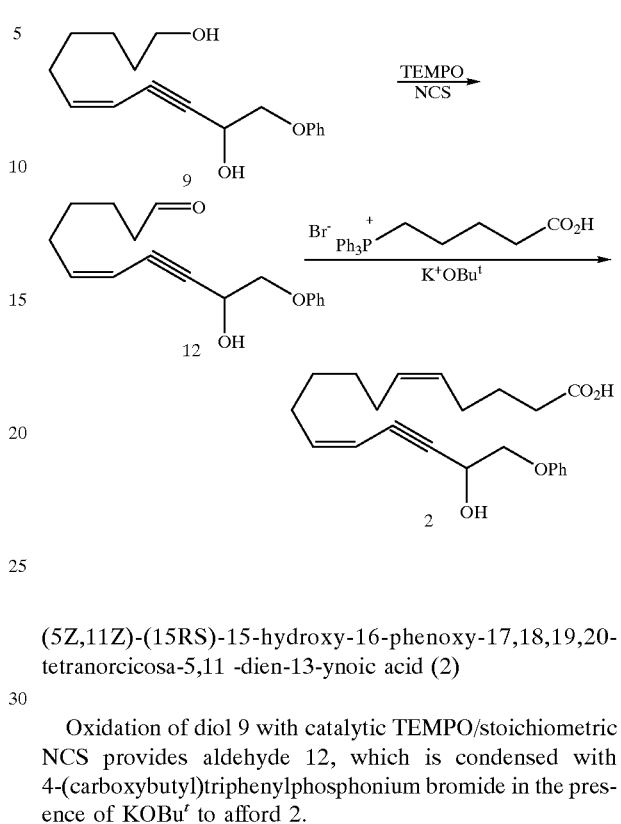

(5Z,11Z)-(15RS)-15-hydroxy-16-phenoxy-17,18,19,20-tetranorcicosa-5,11 -dien-13-ynoic acid (2)

Oxidation of diol 9 with catalytic TEMPO/stoichiometric NCS provides aldehyde 12, which is condensed with 4-(carboxybutyl)triphenylphosphonium bromide in the presence of KOBu$^t$ to afford 2.

EXAMPLE 3

Synthesis of 3

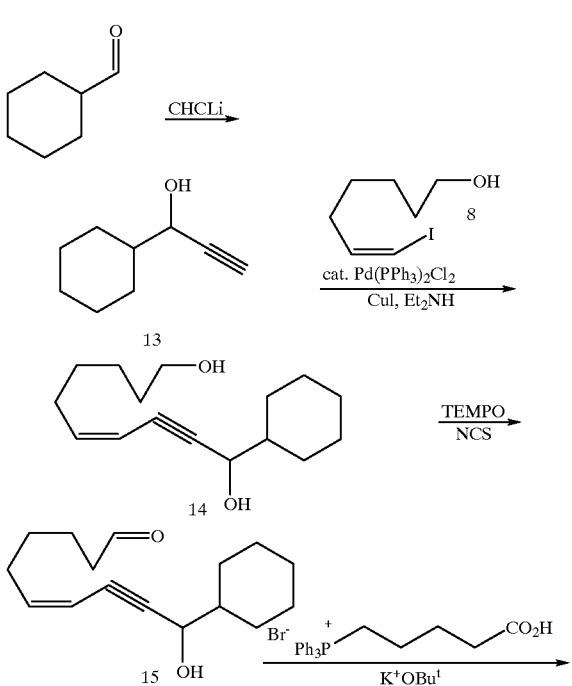

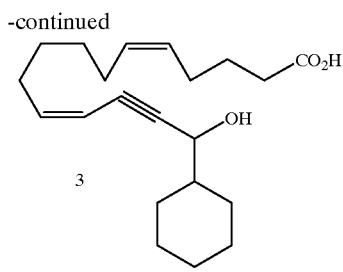

(5Z,11Z)-(15RS)-15-cyclohexyl-15-hydroxy-16,17,18,19, 20-pentanoreicosa-5,11-dien-13-ynoic acid (3)

Addition of cyclohexanecarboxaldehyde to a −78° C. solution of ethynyllithium provides alkynol 13, which is coupled with vinyl iodide 8 under Sonogashira conditions [catalytic $PdCl_2(PPh_3)_2$, catalytic CuI, $Et_2NH$) to give enyne 14. Oxidation of 14 with catalytic TEMPO/stoichiometric NCS yields aldehyde 15, which is condensed with 4-(carboxybutyl)triphenylphosphonium bromide in the presence of $KOBu^t$ to afford 3.

EXAMPLE 4

Synthesis of 4

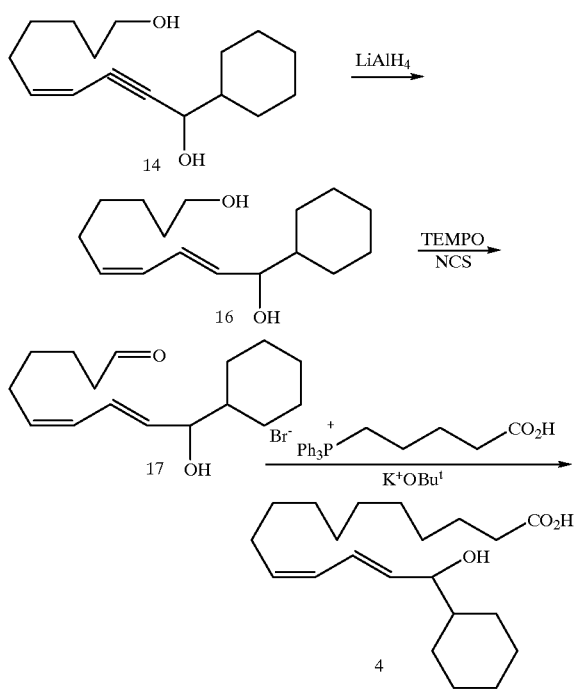

(5Z,11Z,13E)-(15RS)-15-cyclohexyl-15-hydroxyeicosa-5, 11,13-trienoic acid (4)

Reduction of enyne 14 with $LiAlH_4$ affords diene 16, which is oxidized to aldehyde 17 using catalytic TEMPO/ stoichiometric NCS. Wittig condensation of 17 with 4-(carboxybutyl)triphenylphosphonium bromide in the presence of $KOBu^t$ affords 4.

The compounds of the present invention may be contained in various types of pharmaceutical compositions, in accordance with formulation techniques known to those skilled in the art. Preferably, these compounds will be formulated in solutions for topical ophthalmic administration. The level of peroxy compounds in the HETE derivative raw materials that are used to prepare the pharmaceutical formulations of the present invention may have an impact on the HETE derivative's biological activity. Although the precise relationship has not been defined, it is preferable to use HETE derivative raw material supplies containing peroxy compounds at levels no greater than about 0.3 ppm. Methods for determining peroxy levels are known in the art (e.g., European Pharmacopoeia 1997 $3^{rd}$ Ed., Method 2.5.5—Peroxide Value).

The ophthalmic compositions of the present invention will include one or more compounds of the present invention in a pharmaceutically acceptable vehicle. Various types of vehicles may be used. Aqueous solutions are generally preferred, based on ease of formulation, biological compatibility, as well as a patient's ability to easily administer such compositions by means of instilling one to two drops of the solutions in the affected eyes. However, the compounds of the present invention may also be readily incorporated into other types of compositions, such as suspensions, viscous or semi-viscous gels, or other types of solid or semi-solid compositions. Suspensions may be preferred for those compounds of the present invention which are less soluble in water. The ophthalmic compositions of the present invention may also include various other ingredients, such as buffers, preservatives, co-solvents and viscosity building agents.

An appropriate buffer system (e.g., sodium phosphate, sodium acetate or sodium borate) may be added to prevent pH drift under storage conditions.

Antioxidants may be added to compositions of the present invention to protect the active ingredients from oxidation during storage. Examples of such antioxidants include vitamin E and analogs thereof, ascorbic acid and butylated hydroxytoluene (BHT).

Ophthalmic products are typically packaged in multidose form. Preservatives are thus required to prevent microbial contamination during use. Suitable preservatives include: benzalkonium chloride, thimerosal, chlorobutanol, methyl paraben, propyl paraben, phenylethyl alcohol, edetate disodium, sorbic acid, polyquaternium-1, or other agents known to those skilled in the art. Such preservatives are typically employed at a level of from 0.001 to 1.0% weight/volume ("% w/v").

In general, the doses used for the above described purposes will vary, but will be in an effective amount to increase mucin production in the eye and thus eliminate or improve dry eye conditions. As used herein, the term "pharmaceutically effective amount" refers to an amount which improves the dry eye condition in a human patient. When the compositions are dosed topically, they will generally be in a concentration range of from 0.001 to about 1.0% w/v, with 1–2 drops administered 1–4 times per day.

As used herein, the term "pharmaceutically acceptable carrier" refers to any vehicle which, when formulated, is safe, and provides the appropriate delivery for the desired route of administration of an effective amount of at least one compound of the present invention.

In one embodiment, the ophthalmic compositions of the present invention will contain ethanol in addition to a compound of formula (I). As used herein, "an effective concentration of ethanol" refers to a concentration that enhances the biological efficacy of the formula (I) compositions in vivo. In general, the concentration of ethanol necessary for the enhancement of the compounds of formula (I) is believed to be somewhat proportional to the concentration of the formula (I) compound(s) administered. If a relatively high concentration of formula (I) compound(s), e.g., above 0.01% w/v, is administered, the concentration of ethanol in such compositions may be proportionally less than analogous compositions containing lower concentrations of formula (I) compounds. In general, however, the ethanol concentration contained in the ophthalmic compositions of the present invention will range from about 0.001–2% w/v. Compositions containing formula (I) concentrations of about 0.00001–0.02% w/v preferably will contain ethanol in a concentration of about 0.005–0.2% w/v, and most preferably, about 0.02–0.10% w/v. An example of a topically administrable ophthalmic formulation according to this embodiment of the present invention is provided below.

Example 5

| Ingredient | Amount (% w/v) |
|---|---|
| Compound of formula (I) | 0.00001–0.01 |
| Ethanol | 0.0505 |
| Polyoxyl 40 Stearate | 0.1 |
| Boric Acid | 0.25 |
| Sodium Chloride | 0.75 |
| Disodium Edetate | 0.01 |
| Polyquaternium-1 | 0.001 |
| NaOH/HCl | q.s., pH = 7.5 |
| Purified Water | q.s. 100% |

The above composition is prepared by the following method. The batch quantities of polyoxyl 40 stearate, boric acid, sodium chloride, disodium edetate, and polyquaternium-1 are weighed and dissolved by stirring in 90% of the batch quantity of purified water. The pH is adjusted to 7.5±0.1 with NaOH and/or HCl. Under yellow light or reduced lighting, the batch quantity of a compound of formula (I) as a stock solution in ethanol and the additional quantity of ethanol necessary for the batch are measured and added. Purified water is added to q.s. to 100%. The mixture is stirred for five minutes to homogenize and then filtered through a sterilizing filter membrane into a sterile recipient.

Preferably, the above process is performed using glass, plastic or other non-metallic containers or containers lined with such materials.

The invention has been described by reference to certain preferred embodiments; however, it should be understood that it may be embodied in other specific forms or variations thereof without departing from its spirit or essential characteristics. The embodiments described above are therefore considered to be illustrative in all respects and not restrictive, the scope of the invention being indicated by the appended claims rather than by the foregoing description.

What is claimed is:

1. A compound of formula I:

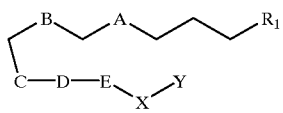

I wherein:
R$^1$ is CO$_2$R, CONR$^2$R$^3$, CH$_2$OR$^4$, CH$_2$NR$^5$R$^6$, CH$_2$N$_3$, CH$_2$Hal, CH$_2$NO$_2$, CH$_2$SR$^{20}$, COSR$^{21}$, or 2,3,4,5-tetrazol-1-yl, where:
R is H or a pharmaceutically acceptable cation, or CO$_2$R forms a pharmaceutically acceptable ester moiety;
NR$^2$R$^3$, NR$^5$R$^6$ are the same or different and comprise a free or functionally modified amino group;
OR$^4$ comprises a free or functionally modified hydroxy group; Hal is F, Cl, Br, or I;
SR$^{20}$ comprises a free or functionally modified thiol group;
R$^{21}$ is H or a pharmaceutically acceptable cation, or COSR$^{21}$ forms a pharmaceutically acceptable thioester moiety;

A, B, C, D are the same or different and are C$_1$–C$_5$ alkyl, C$_2$–C$_5$ alkenyl, C$_{1-5}$ cyclopropyl, C$_2$–C$_5$ alkynyl, or a C$_3$–C$_5$ allenyl group;
E is

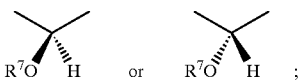

where OR$^7$ comprises a free or functionally modified hydroxy group;
X=(CH$_2$)$_m$ or (CH$_2$)$_m$O, where m=1–6; and
Y=a phenyl ring optionally substituted with alkyl, halo, trihalomethyl, acyl, or a free or functionally modified hydroxy, amino, or thiol group; or
X—Y (CH$_2$)$_p$Y$^1$; where p=0–6; and

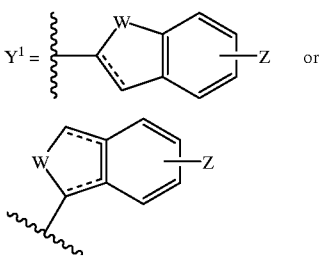

wherein:
W=CH$_2$, O, S(O)$_q$, NR$^8$, CH$_2$CH$_2$, CH=CH, CH$_2$O, CH$_2$S(O)q, CH=N, or CH$_2$NR$^8$; where q=0–2, and R$^8$=H, alkyl, or acyl;
Z=H, alkyl, acyl, halo, trihalomethyl, or a free or functionally modified amino, thiol, or hydroxy group; and
----=single or double bond;
or X—Y=cyclohexyl.

2. The compound of claim 1, wherein:
R$^1$ is CO$_2$R, where R is H or an ophthalmically acceptable cationic salt, or CO$_2$R forms an ophthalmically acceptable ester moiety;
A, B, C, D are the same or different and are CH$_2$CH$_2$, CH=CH, C≡C, or

E is

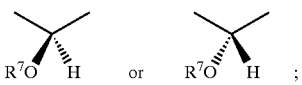

where R$^7$ is H or CH$_3$;
X is CH$_2$CH$_2$ or CH$_2$O; and
Y phenyl, optionally substituted with halo, trifluoromethyl, or a free or functionalized hydroxy group; or
X—Y=cyclohexyl; or X—Y=Y¹,
Y¹ = 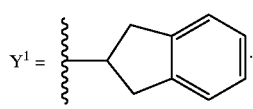.
3. The compound of claim 1, wherein the compound is selected from the group consisting of:
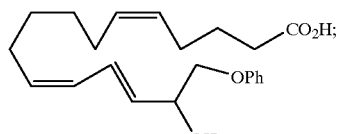
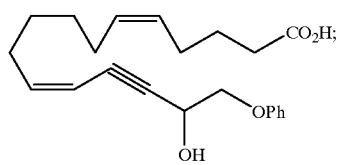
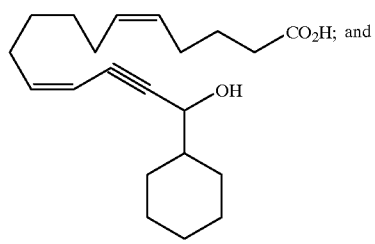
-continued
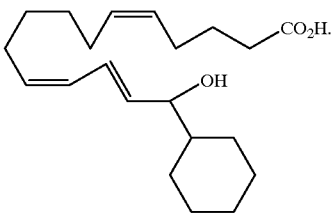
4. The compound of claim 1, wherein the compound is selected from the group consisting of:
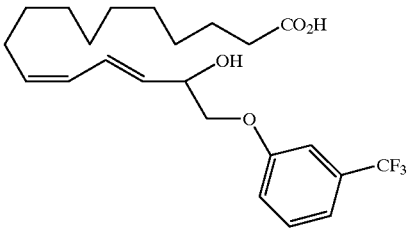
and
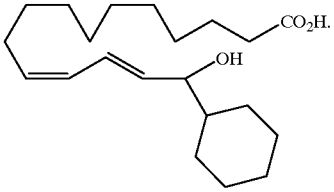
* * * * *